United States Patent
Holmes-Farley et al.

(10) Patent No.: US 6,203,785 B1
(45) Date of Patent: Mar. 20, 2001

(54) POLY(DIALLYLAMINE)-BASED BILE ACID SEQUESTRANTS

(75) Inventors: Stephen Randall Holmes-Farley, Arlington; Pradeep K. Dhal; John S. Petersen, both of Acton, all of MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 08/777,408

(22) Filed: Dec. 30, 1996

(51) Int. Cl.$^7$ .......................... A61K 31/787; A61P 3/06
(52) U.S. Cl. ........................... 424/78.18; 424/78.35; 514/824
(58) Field of Search ............... 424/78.19, 78.22, 424/78.23, 78.35, 78.36, 78.27, 78.29; 514/824; 525/328.3; 526/310

(56) References Cited

U.S. PATENT DOCUMENTS

| | | | |
|---|---|---|---|
| 2,874,132 | 2/1959 | Reiner . | |
| 3,288,770 | 11/1966 | Butler ................................. | 260/88.3 |
| 3,308,020 | 3/1967 | Wolf et al. ............................. | 167/65 |
| 3,383,281 | 5/1968 | Wolf et al. ............................. | 167/65 |
| 3,562,266 | 2/1971 | Minisci et al. . | |
| 3,585,118 | 6/1971 | Harada et al. .................. | 204/159.22 |
| 3,692,895 | 9/1972 | Nelson et al. ......................... | 424/78 |
| 3,780,171 | 12/1973 | Irmscher et al. ...................... | 424/79 |
| 3,787,474 | 1/1974 | Daniels et al. ........................ | 260/459 |
| 3,801,641 | 4/1974 | Payot et al. . | |
| 3,803,237 | 4/1974 | Lednicer et al. .................. | 260/584 R |
| 3,833,531 | 9/1974 | Keim ................................. | 260/29.6 |
| 3,840,504 | 10/1974 | Keim ................................. | 260/79.3 |
| 3,980,770 | 9/1976 | Ingelman et al. ..................... | 424/79 |
| 4,027,009 | 5/1977 | Grier et al. ............................ | 424/78 |
| 4,071,478 | 1/1978 | Shen et al. ........................ | 260/2 R |
| 4,098,726 | 7/1978 | Wagner et al. ...................... | 528/403 |
| 4,101,461 | 7/1978 | Strop et al. ............................ | 521/32 |
| 4,111,859 | 9/1978 | Strop et al. ............................ | 521/33 |
| 4,205,064 | 5/1980 | Wagner et al. ...................... | 424/78 |
| 4,217,429 | 8/1980 | Wagner et al. ...................... | 525/411 |
| 4,287,172 | 9/1981 | Jacquet et al. ......................... | 424/47 |
| 4,340,585 | 7/1982 | Borzatta et al. ....................... | 424/79 |
| 4,360,434 | 11/1982 | Kawaguchi et al. .............. | 210/500.2 |
| 4,426,489 | 1/1984 | Wessling et al. ..................... | 524/815 |
| 4,540,760 | 9/1985 | Harada et al. ........................ | 526/211 |
| 4,557,930 | 12/1985 | Kihara et al. .......................... | 424/79 |
| 4,559,391 | 12/1985 | Ueda et al. ............................ | 525/366 |
| 4,605,701 | 8/1986 | Harada et al. ........................ | 525/107 |
| 4,680,360 | 7/1987 | Ueda et al. ............................ | 526/310 |
| 4,759,923 | 7/1988 | Buntin et al. ......................... | 424/440 |
| 4,812,540 | 3/1989 | Kageno et al. ..................... | 526/218.1 |
| 5,055,197 | 10/1991 | Albright et al. ...................... | 210/638 |
| 5,185,411 | 2/1993 | Jueptner et al. ...................... | 526/200 |
| 5,189,111 | 2/1993 | Danner ............................. | 525/328.2 |
| 5,236,701 | 8/1993 | St. Pierre et al. ..................... | 424/78 |
| 5,374,422 | 12/1994 | St. Pierre et al. ................. | 424/78.12 |
| 5,414,068 | 5/1995 | Bliem et al. .......................... | 528/288 |
| 5,428,112 | 6/1995 | Ahlers et al. ..................... | 525/326.7 |
| 5,430,110 | 7/1995 | Ahlers et al. ...................... | 525/328.2 |
| 5,451,397 | 9/1995 | Albright et al. .................. | 424/78.01 |
| 5,462,730 | 10/1995 | McTaggart et al. ............... | 424/78.35 |

FOREIGN PATENT DOCUMENTS

| | | |
|---|---|---|
| 0 081 291 A3 | 6/1983 | (EP) . |
| 0 162 388 | 11/1985 | (EP) . |
| 0 280 445 | 8/1988 | (EP) . |
| 0 373 852 A2 | 6/1990 | (EP) . |
| 0 401 705 | 12/1990 | (EP) . |
| 0432995A1 | 6/1991 | (EP) . |
| 0 459 632 A1 | 12/1991 | (EP) . |
| 798488 | 7/1958 | (GB) . |
| 929391 | 6/1963 | (GB) . |
| 1567294 | 5/1980 | (GB) . |
| 2 090 605 | 7/1982 | (GB) . |
| 2 227 663 | 8/1990 | (GB) . |
| 56-010531 | 2/1981 | (JP) . |
| 57-047302 | 3/1982 | (JP) . |
| 57-125233 | 8/1982 | (JP) . |
| 62-170591 | 7/1987 | (JP) . |
| 62-257481 | 11/1987 | (JP) . |
| 02001358 | 1/1990 | (JP) . |
| WO91/18027 | 11/1991 | (WO) . |
| WO92/10522 | 6/1992 | (WO) . |
| WO94/04596 | 3/1994 | (WO) . |
| WO94/27620 | 12/1994 | (WO) . |
| WO95/34585 | 12/1995 | (WO) . |
| WO95/34588 | 12/1995 | (WO) . |

OTHER PUBLICATIONS

McLean, C.D., et al., "Cyclopolymerization. VI. Preparation and Properties of Crosslinked Polyamines by Cyclopolymerization," *J. Macromol. Sci.–Chem.*, A10(5):857–873 (1976).

Bolto, B.A., et al., "Synthesis of Cross–Linked Polyallylamines Which are Resistant to Sulfite Attack," *J. Macromol. Sci.–Chem.*, A17(1):153–166 (1982).

Heming, A.E. and Flanagan, Thomas L., "Considerations in the Selection of Cation Exchange Resins for Therapeutic Use," *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

(List continued on next page.)

*Primary Examiner*—Edward J. Webman
(74) *Attorney, Agent, or Firm*—Hamilton, Brook, Smith & Reynolds, P.C.

(57) ABSTRACT

The present invention relates to a method for removing bile acids from a patient and certain polymers of use in the method. The method comprises the step of administering to the patient a therapeutically effective amount of a polymer composition which includes a a poly(diallylamine) polymer which is substituted with hydrophobic groups. The hydrophobic groups can be a substituted or unsubstituted, straight chain or branched $C_3$–$C_{24}$-alkyl group, an aralkyl group or an aryl group.

37 Claims, No Drawings

OTHER PUBLICATIONS

Butler, G.B. and Do, C.H., "Comblike Cyclopolymers of Alkyldiallylamines and Alkyldiallylmethylammonium Chlorides," in *Water–Soluble Polymers*, eds. Shalaby, McCormick & Butler, Chapter 9, pp. 151–158 ACS Symposium Series 467 (1991).

Dubin, P.L. and Davis, D.D., "Quasi–Elastic Light Scattering of Polyelectrolyte–Micelle Complexes," *Macromolecules 17*: 1294–1296 (1984).

Wang, G.–J. and Engberts, J., "Fluorescence probing of the formation of hydrophobic microdomains by cross–linked poly(alkylmethyldiallylammonium bromides) in aqueous solution," *Recl. Trav. Chim. Pays–Bas 113*:390–393 (1994).

Kunitake, T., et al., "Catalyses of Polymer Complexes. 4. Polysoap–Catalyzed Decarboxylation of 6–Nitrobenzisoxazole–3–carboxylate Anion. Importance of the Hydrophobic Environment in Activation of the Anion," *J. Org. Chem 42*(2): 306–312 (1977).

Wang, G.–J. and Engberts, J., "Study of the Conformational State of Non–Cross–Linked and Cross–Linked Poly(alkylmethyldiallylammonium Chlorides) in Aqueous Solution by Fluorescence Probing," *Gazzetta Chimica Italiana*, 125: 393–397 (1995).

Kuron, G.W., et al., "The Bile Acid Binding and Hypocholesterolemic Action of Two Water–Soluble Polymers," *Atherosclerosis*, 37 353–360 (1980).

Harada, S. and Arai, K., "The Cyclo–copolymerization of Diallyl Compounds and Sulfur Dioxide," *Die Makromolekulare Chemie 107*: 64–93 (1967).

Wang, G.–J. and Engberts, J., "Induction of Aggregate Formation of Cationic Polysoaps and Surfactants by Low Concentrations of Additives in Aqueous Solution," *Langmuir*, 10(8): 2583–2587 (1994).

Wang, G.–J. and Engberts, J., "Synthesis of Hydrophobically and Electrostatically Modified Polyacrylamides and Their Catalytic Effects on the Unimolecular Decarboxylation of 6–Nitrobenzisoxazole–3–carboxylate Anion," *Langmuir*, 11(10): 3856–3861 (1995).

Wang, G.–J. and Engberts, J., "Synthesis and Catalytic Properties of Non–Cross–Linked and Cross–Linked Poly(alkylmethyldiallylammonium bromides) Having Decyl, Octyl, and Hexyl Side Chains," *J. Org. Chem*, 60: 4030–4038 (1995).

Kevelam, J., et al., "Polymer–Surfactant Interactions Studied by Titration Microcalorimetry: Influence of Polymer Hydrophobicity, Electrostatic Forces, and Surfactant Aggregational State," *Langmuir*, 12(20): 4709–4717 (1996).

Wang, G.–J. and Engberts, J., "Synthesis and Catalytic Properties of Cross–Linked Hydrophobically Associating Poly(alkylmethyldiallylammonium bromides)," *J. Org. Chem.*, 59(15): 4076–4081 (1994).

Yang, Y.J. and Engberts, J., "Synthesis and Catalytic Properties of Hydrophobically Modified Poly(alkylmethyldiallylammonium bromides)," *J. Org. Chem.*, 56: 4300–4304 (1991).

Negi, Y., et al., "Cyclopolymerization of Diallylamine Derivatives in Dimethyl Sulfoxide," *J. of Polymer Science*: Part A–1, 5: 1951–1965 (1967).

Hodgkin, H. et al., "Use of $^{13}$C–NMR in the Study of Reactions on Crosslinked Resins," Published by John Wiley & Sons, *J. of Polymer Science: Polymer Chemistry Edition*, 19(5): 1239–1249 (1981).

Yeh, F., et al., "Nanoscale Supramolecular Structures in the Gels of Poly(Diallyldimethylammonium Chloride) Interacting with Sodium Dodecyl Sulfate," *J. Am. Chem. Soc.*, 118(28): 6615–6618 (1996).

Boothe, J.E., et al., "Some Homo– and Copolymerization Studies of Dimethyldiallylammonium Chloride," *J. Macromol. Sci.–Chem.*, A4(6): 1419–1430 (1970).

POLY(DIALLYLAMINE)-BASED BILE ACID SEQUESTRANTS

BACKGROUND OF THE INVENTION

Salts of bile acids act as detergents to solubilize and, consequently, aid in the digestion of, dietary fats. Bile acids are derived from cholesterol. Following digestion, bile acids can be passively absorbed in the jejunum or reabsorbed by active transport in the ileum. Bile acids which are not reabsorbed are deconjugated and dehydroxylated by bacterial action in the distal ileum and large intestine.

Reabsorption of bile acids from the intestine conserves lipoprotein cholesterol in the bloodstream. Conversely, the blood cholesterol level can be reduced by hindering reabsorption of bile acids.

One method of reducing the amount of bile acids that are reabsorbed is oral administration of compounds that sequester the bile acids and cannot themselves be absorbed. The sequestered bile acids consequently are excreted. Serum cholesterol is then employed to produce more bile acids, thereby lowering the serum cholesterol level of the patient.

SUMMARY OF THE INVENTION

The present invention relates to a method for removing bile acids from a patient as well as certain polymers for use in the method. The method comprises the step of administering to the patient a therapeutically effective amount of a polymer characterized by a diallylamine monomer wherein the amino nitrogen atom bears at least one hydrophobic substituent. The hydrophobic substituent can be a substituted or unsubstituted, straight chain or branched $C_3$–$C_{24}$-alkyl group, a substituted or unsubstituted arylalkyl group or a substituted or unsubstituted aryl group. The polymer to be administered can be hoinopolymer or a copolymer.

In one embodiment, the polymer to be administered is a crosslinked or linear poly(diallylamine) polymer wherein at least 10% of the amino nitrogen atoms are substituted by a $C_3$–$C_{24}$-alkyl group. In another embodiment, the polymer to be administered is characterized by a diallylamine monomer wherein the amino nitrogen atom bears an alkyl group which is substituted with a quaternary ammonium group. The nitrogen atom of the ammonium group can bear at least one terminal hydrophobic substituent.

The polymer to be administered can comprise secondary amino groups, tertiary amino groups or quaternary ammonium groups or a combination thereof. Polymers which comprise secondary or tertiary amino groups can also be administered in the form of salts of a pharmaceutically acceptable acid.

The polymer can be linear or crosslinked. In one embodiment, the polymer is crosslinked via the incorporation of a multifunctional comonomer. In another embodiment, the polymer is crosslinked via bridging groups which link amino nitrogen atoms on different polymer strands.

In another embodiment, the invention relates to poly (diallylamine) polymers which are useful as bile acid sequestrants. These polymers are characterized by an diallylamine monomer, or repeat unit, wherein the amino nitrogen bears an alkyl substituent which is substituted with an ammonium group. The polymer can be a homopolymer or a copolymer.

The present invention offers the advantage that both substituted and unsubstituted diallylamines are readily polymerized and crosslinked, in comparison to other amine monomers. Such polymers also provide improved efficacy over polymers utilized in prior art methods.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principal features of the invention can be employed in various embodiments without departing from the scope of the present invention.

The present invention is based on Applicants' discovery that poly(diallylamine) polymers comprising hydrophobic groups exhibit excellent bile acid sequestration activity. The invention provides a method for removing bile acids from a patient comprising administering to the patient a therapeutically effective amount of a polymer characterized by a diallylamine monomer, or repeat unit, wherein the amino nitrogen atom bears a hydrophobic substituent.

As used herein, the term "therapeutically effective amount" refers to an amount which is sufficient to remove a significant quantity of bile acids from the patient and, thus, to lower the serum cholesterol level of the patient. The patient can be an animal, for example, a mammal, or a human.

A "hydrophobic substituent", as the term is used herein, is a moiety which, as a separate entity, is more soluble in octanol than water. For example, the octyl ($C_8H_{17}$) group is hydrophobic because its parent alkane, octane, has greater solubility in octanol than in water. The hydrophobic substituent can be a saturated or unsaturated, substituted or unsubstituted hydrocarbon group. Such groups include susbstituted and unsubstituted, normal, branched or cyclic alkyl groups having 3 or more carbon atoms, substituted or unsubstituted arylalkyl or heteroarylalkyl groups and substituted or unsubstituted aryl or heteroaryl groups.

In one embodiment, the polymer to be administered is a poly(diallylamine) polymer characterized by a diallylamine monomer wherein the amino nitrogen atom bears at least one hydrophobic substituent selected from the group consisting of substituted or unsubstituted, normal, branched or cyclic $C_3$–$C_{24}$-alkyl groups, such as a hexyl, heptyl, octyl, nonyl, decyl, undecyl, dodecyl, tridecyl or tetradecyl group; substituted or unsubstituted $C_3$–$C_{24}$-alkenyl groups, such as propenyl group; substituted or unsubstituted arylalkyl groups, such as a benzyl group; and substituted or unsubstituted aryl groups, such as a phenyl or naphthyl group. Suitable alkyl substituents include halo (e.g. fluoro, chloro, bromo or iodo) groups, and alkoxy, cycloalkyl, substituted and unsubstituted, quaternary, amido, sulfone, sulfoxide, alkoxy and aryl groups. Suitable aryl and arylalkyl substituents include fluoro, chloro, bromo, iodo, amino, ammonioalkyl, alkyl, alkoxy, hydroxy, alkoxy, sulfoxide and sulfone groups.

In one embodiment, at least 10% of the amino nitrogen atoms within the polymer to be administered bear a hydrophobic substituent, such as a $C_2$–$C_{24}$-alkyl group. Preferably at least about 20% of the amino nitrogen atoms bear a hydrophobic substituent. In other embodiments, at least about 40% of the amino nitrogen atoms can bear a hydrophobic substituent.

In general, poly(diallylamine) polymers are characterized by monomers, or repeat units, comprising five-membered rings, monomers comprising six-membered rings, or a combination thereof. In one embodiment, the polymer to be administered is characterized by an ammonium-bearing monomer of Formula I or of Formula II

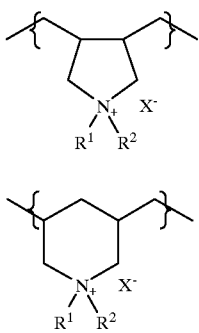

(I)

(II)

or a combination thereof, wherein $R^1$ is a hydrophobic substituent, as described above, and $R^2$ is hydrogen, methyl, or a hydrophobic substituent. In a preferred embodiment, $R^1$ is selected from among the octyl, decyl and dodecyl groups and $R^2$ is methyl.

X is an anion, such as the conjugate base of a pharmaceutically acceptable acid. Such anions include chloride, citrate, tartrate, lactate, phosphate, hydrophosphate, methanesulfonate, acetate, formate, maleate, fumarate, malate, succinate, malonate, sulfate, hydrosulfate, L-glutamate, L-aspartate, pyruvate, mucate, benzoate, glucuronate, oxalate, ascorbate and acetylglycinate. In a preferred embodiment, $X^-$ is chloride.

In another embodiment, the polymer to be administered is characterized by an amine-bearing monomeric unit of Formula III or Formula IV

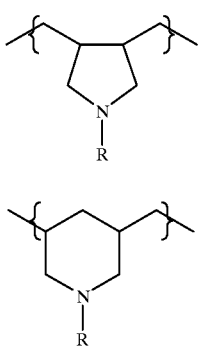

(III)

(IV)

or a combination thereof, wherein R is a hydrophobic substituent as previously described.

In a preferred embodiment, the polymer to be administered comprises one or more monomers of Formulas I–IV wherein at least 10%, preferably at least about 20%, of the amino nitrogen atoms bear a $C_3$–$C_{24}$-alkyl substituent. Examples of particularly preferred $C_3$–$C_{24}$-alkyl groups include hexyl, heptyl, octyl, nonyl, decyl, undecyl, dodecyl, tridecyl and tetradecyl groups.

The polymer to be administered can be a copolymer comprising one or more diallylamine monomers, such as one or more monomers of Formulas I, II, III, and IV, and at least one additional monomer. In one embodiment, the additional monomer is sulfur dioxide. In polymers comprising sulfur dioxide, the polymer backbone includes —$SO_2$— units between pairs of diallylamine monomers.

In a further embodiment, the invention provides a method for removing bile acids from a patient comprising the step of administering to the patient a therapeutically effective amount of a polymer characterized by a diallylamine repeat unit wherein the amino nitrogen atom bears an ammonioalkyl substituent. The invention also includes the ammonioalkyl-substituted polymers which are of use in this method.

The term "ammonioalkyl", as used herein, refers to an alkyl group which is substituted by a nitrogen atom bearing three additional substituents. Thus, the nitrogen atom is an ammonium nitrogen atom which bears an alkylene substituent, which links this atom to the diallylamine nitrogen atom, and three additional substituents selected from among hydrogen, alkyl and arylalkyl. An ammonioalkyl group will further include a negatively charged counter ion, such as a conjugate base of a pharmaceutically acceptable acid.

The diallylamine repeat unit can be, for example, of Formula I, Formula II, Formula III, or Formula IV, wherein at least one of the nitrogen substituents is an ammonioalkyl substituent. Suitable ammonioalkyl substituents are of the general formula

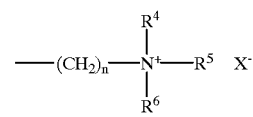

wherein $R^4$, $R^5$ and $R^6$ are each, independently, a hydrogen atom or a $C_1$–$C_{24}$ alkyl group; n is an integer from 2 to about 20, preferably from 3 to about 6; and $X^-$ is an anion, such as a conjugate base of a pharmaceutically acceptable acid. Preferably, at least one of $R^4$, $R^5$ and $R^6$ is a hydrophobic group such as a $C_3$–$C_{24}$-alkyl group. More preferably, at least one of $R^4$, $R^5$ and $R^6$ is a $C_6$–$C_{24}$-alkyl group. Suitable examples of ammonioalkyl groups include, but are not limited to, 4-(dioctylmethylammonio)butyl;
3-(dodecyldimethylammonio)propyl;
3-(octyldimethylammonio)propyl;
3-(decyldimethylammonio)propyl;
5-(dodecyldimethylammonio)pentyl;
3-(cyclohexyldimethylammonio)propyl;
3-(decyldimethylammonio)-2-hydroxypropyl;
3-(tridecylammonio)propyl;
3-(docosyldimethylammonio)propyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
3-(dimethylundecylammonio)propyl; and
3-(tetradecyldimethylammonio)propyl.

The polymer can be a homopolymer which comprises only a monomer selected from among Formulas I–IV, above, wherein the nitrogen atom bears at least one ammonioalkyl substituent. The polymer can also be a copolymer which comprises a monomer of this type and at least one additional monomer. For example, the polymer can comprise a second diallylamine monomer wherein the nitrogen atom bears a substituent selected from among hydrogen, methyl, ethyl, hydrophobic groups and ammonioalkyl groups.

The polymer can also comprise an additional monomer which is not a diallylamine. Suitable examples of additional polymers include substituted and unsubstituted acrylate, acrylamide, methacrylate, methacrylamide, allylamine, allyl alcohol, vinyl amine and vinyl alcohol. for example, the additional monomer can be a substituted acrylate or acrylamide which bears a hydrophobic group, such as a $C_3$–$C_{24}$-alkylacrylate or an N–$C_3$–$C_{24}$–alkylacrylamide. The additional monomer can also be a hydrophilic monomer, such as N-(2-hydroxyethyl)acrylamide or (3-hydroxypropyl) acrylate. Also included are the multifunctional crosslinking co-monomers which are discussed in detail below.

The copolymers can have a wide range of compositions. Typically, the ammonioalkyl-substituted diallylamine monomer will constitute from about 10% to about 90% of the monomeric units composing the polymer.

The polymers of use in the present method can be linear or crosslinked. The polymer can be crosslinked, for example, by the incorporation within the polymer of a multifunctional comonomer. Suitable multifunctional comonomers include diacrylates, triacrylates and tetraacrylates, dimethacrylates, diacrylamides, diallylacrylamide and di(methacrylamides). Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene. The amount of crosslinking agent is typically between 1.0% and 25% by weight relative to the weight of the polymer, preferably from about 2.5% to about 20% by weight and more preferably from about 2% to about 12% by weight.

The polymer can also be crosslinked by bridging units which link amino groups on adjacent polymer strands. Suitable bridging units include straight chain or branched, substituted or unsubstituted alkylene groups, diacylalkylene groups, diacylarene groups and alkylene bis(carbamoyl) groups. Examples of suitable bridging units include —$(CH_2)_n$—, wherein n is an integer from about 2 to about 20; —$CH_2$—$CH(OH)$—$CH_2$—; —$C(O)CH_2CH_2C(O)$—; —$CH_2$—$CH(OH)$—O—$(CH_2)_n$—O—$CH(OH)$—$CH_2$—, wherein n is 2 to about 4; —$C(O)$—$(C_6H_2(COOH)_2)$—$C(O)$— and —$C(O)NH(CH_2)_pNHC(O)$—, wherein p is an integer from about 2 to about 20.

Advantageously, crosslinking the polymers renders the polymers non-adsorbable and stable in the patient. A "stable" polymer composition, when administered in therapeutically effective amounts, does not dissolve or otherwise decompose to form potentially harmful byproducts, and remains substantially intact.

Polymers of use in the present method are, preferably, of a molecular weight which enables them to reach and remain in the gastrointestinal tract for a sufficient period of time to bind a significant amount of one or more bile acids. The polymers should, thus, be of sufficiently high molecular weight to resist, partially or completely, absorption from the gastrointestinal tract into other regions of the body. The resulting polymer/bile salt complex should then be excreted from the body. Suitable linar (non-crosslinked) polymers have molecular weights which range from about 2,000 Daltons to about 500,000 Daltons, preferably from about 5,000 Daltons to about 150,000 Daltons. Crosslinked polymers, however, are not generally chaacterized by molecular weight. The crosslinked polymers discussed herein should be sufficiently crosslinked to resist adsorption from the gastrointestinal tract.

The polymer network can be administered orally to a patient in a dosage of about 1 mg/kg/day to about 10 g/kg/day; the particular dosage will depend on the individual patient (e.g., the patient's weight and the extent of bile salt removal required). The polymer can be administered either in hydrated or dehydrated form, and can be flavored or added to a food or drink, if desired, to enhance patient acceptance. Additional ingredients such as other bile acid sequestrants, drugs for treating hypercholesterolemia, atherosclerosis or other related indications, or inert ingredients, such as artificial coloring agents, may be added as well.

Examples of suitable forms for administration include pills, tablets, capsules, and powders (i.e. for sprinkling on food). The pill, tablet, capsule or powder can be coated with a substance capable of protecting the composition from the gastric acid in the patient's stomach for a period of time sufficient for the composition to pass undisintegrated into the patient's small intestine. The polymer can be administered alone or in combination with a pharmaceutically acceptable carrier, diluent or excipient substance, such as a solid, liquid or semi-solid material. Examples of suitable carriers, diluents and excipients include lactose, dextrose, sucrose, sorbitol, mannitol, starches, gum acacia, alginates, tragacanth, gelatin, calcium silicate, cellulose and others known in the art.

Polymers of use in the present method can be prepared using techniques known in the art of polymer synthesis (see for example, Shalaby et al., ed., *Water-Soluble Polymers*, American Chemical Society, Washington D.C. (1991)). For example, the appropriate monomer can be polymerized by methods known in the art, for example, via a free radical addition process. In this case the polymerization mixture includes a free-radical initiator, such as a free radical initiator selected from among those which are well known in the art of polymer chemistry. Suitable free-radical initiators include azobis(isobutyronitrile), azobis(4-cyanovaleric acid), azobis(amidinopropane) dihydrochloride, potassium persulfate, ammonium persulfate and potassium hydrogen persulfate. The free radical initiator is preferably present in the reaction mixture in an amount ranging from about 0.1 mole percent to about 5 mole percent relative to the monomer.

The polymer can be crosslinked, for example, by including a multifunctional co-monomer as the crosslinking agent in the reaction mixture. A multifunctional co-monomer can be incorporated into two or more growing polymer chains, thereby crosslinking the chains. Suitable multifunctional co-monomers include those discussed above. The amount of crosslinking agent added to the reaction mixture is, generally, between 1.0% and 25% by weight relative to the combined weight of the polymer and the crosslinking agent, and preferably from about 2.5% to about 20% by weight.

The multifunctional co-monomer can also take the form of a multifunctional diallylamine, such as a bis (diallylamino)alkane or a bis(diallylalkylammonio) alkane. Suitable monomers of this type include 1,10-bis (diallylmethylammonio)decane dibromide and 1,6-bis (diallylmethylammonio)hexane, each of which can be formed by the reaction of diallylmethylamine with the appropriate dibromoalkane.

The polymers to be administered can also be crosslinked subsequent to polymerization by reacting the polymer with one or more crosslinking agents having two or more functional groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include epichlorohydrin, succinyl dichloride, butanedioldiglycidyl ether, ethanedioldiglycidyl ether, pyromellitic dianhydride and dihaloalkanes. The crosslinking agent cn also be an $\alpha,\omega$-alkylene diisocyanate, for example $OCN(CH_2)_pNCO$, wherein p is an integer from about 2 to about 20. The polymer can be reacted with an amount of crosslinking agent equal from about 0.5 and 20 mole percent relative to the amino groups within the polymer, depending upon the extent of crosslinking desired.

A polymer comprising alkylated amino groups can be formed by reacting a preformed polymer with a suitable alkylating agent, or by polymerizing an alkylated monomer. Suitable alkylated monomers can be prepared by reacting diallylamine or a diallylamine derivative, such as diallylmethylamine, with an alkylating agent. As used herein, the term "alkylating agent" refers to a compound which reacts with an amino group to form a nitrogen-carbon bond, thereby adding an alkyl or alkyl derivative substituent to the nitrogen atom. Suitable alkylating agents are compounds comprising an alkyl group or alkyl derivative which is bonded to a leaving group, such as a halo, tosylate, mesylate or epoxy group. Examples of preferred alkylating agents include $C_1$–$C_{24}$-alkyl halides, for example, n-butyl halides, n-hexyl halides, n-decyl halides, and n-octadecyl halides; $C_2$–$C_{24}$-dihaloalkanes, for example, 1,10-dihalodecanes; $C_1$–$C_{24}$-hydroxyalkyl halides, for example, 11-halo-1-undecanols; $C_1$–$C_{24}$-arylalkyl halides, for example, benzyl halide; $C_2$–$C_{24}$-alkylepoxy ammonium salts, for example, glycidylpropyl-trimethylammonium salts; and $C_2$–$C_{24}$-epoxyalkylamides, for example, N-(2,3-epoxypropyl)butyramide or N-(2,3-epoxypropyl) hexanamide. Preferred alkylating agents include halodecane, and halododecane, where in each case "halo" represents a chloro, bromo or iodo substituent.

Diallylamine polymers having amino groups which bear quaternary ammonium-substituted alkyl groups can be prepared using alkylating agents such as (X-alkyl)ammonium salts, wherein X represents a suitable leaving group, as described above. These compounds can be prepared by the reaction of an appropriate dihaloalkane, such as a bromochloroalkane, with a tertiary amine. Suitable alkylating agents of this type include the following:

(4-bromobutyl)dioctylmethylammonium bromide;
(3-bromopropyl)dodecyldimethylammonium bromide;
(3-chloropropyl)dodecyldimethylammonium bromide);
(3-bromopropyl)octyldimethylammonium bromide;
(3-chloropropyl)octyldimethylammonium bromide;
(3-iodobutyl)dioctylmethylammonium bromide;
(2,3-epoxypropyl)decyldimethylammonium bromide;
(3-chloropropyl)decyldimethylammonium bromide;
(5-tosylpentyl)dodecyldimethylammonium bromide;
(6-bromohexyl)octyldimethylammonium bromide;
(12-bromododecyl)decyldimethylammonium bromide;
(3-bromopropyl)tridecylammonium bromide;
(3-bromopropyl)docosyldimethylammonium bromide;
(6-bromohexyl)docosyldimethylammonium bromide;
(4-chlorobutyl)dodecyldimethylammonium bromide;
(3-chloropropyl)octadecyldimethylammonium bromide;
(3-chloropropyl)hexyldimethylammonium bromide;
(3-chloropropyl) methyldioctylammonium bromide;
(3-chloropropyl)methyldidecylammonium bromide;
(3-chloropropyl)cyclohexyldimethylammonium bromide;
(3-bromopropyl)heptydimethylammonium bromide;
(3-bromopropyl)dimethylnonylammonium bromide;
(6-bromohexyl) dimethylundecylammonium bromide;
(4-chlorobutyl)heptyldimethylammonium bromide;
(3-chloropropyl)dimethylundecylammonium bromide; and
(3-chloropropyl)tetradecyldimethylammonium bromide.

Each of the alkylating agents described above can also exist and be used as a salt in combination with an anion other than bromide. For example, these and similar alkylating agents can be prepared and used as salts with a wide range of anions, including chloride, iodide, acetate, p-toluenesulfonate and methanesulfonate.

When the hydrophobic groups are added to the polymer by way of an alkylating agent as described above, the extent of alkylation can be determined by methods which are well known in the chemical arts. The increase in polymer mass due to alkylation provides one measure of the extent of alkylation. For example, in a reaction between poly (diallylmethylamine) and 1-bromodecane, a product/starting material mass ratio of about 3.0, 2.0 and 1.5 represent approximately 100%, 50% and 25% alkylation, respectively. The degree of alkylation can also be determined by elemental analysis of the product polymer. In this case, the carbon/nitrogen (C/N) mass ratio is a direct measure of the degree of alkylation. For example, the reaction of poly (diallylmethylamine) with 1-bromodecane yields a product with a higher C/N mass ratio than that of the starting polymer. Product C/N mass ratios of about 6, 8.2, 10.6 and 14.6 represent, approximately, 0%, 25%, 50% and 100% alkylation, respectively.

The invention will now be further and specifically described by the following examples.

EXAMPLES

Example 1

Synthesis of Diallylmethyldodecylammonium bromide

To a 2 L Morton flask was added diallylmethylamine (100 g), 1-bromododecane (249 g), and tetrahydrofuran (750 mL). The mixture was heated to 65° C. for 44 h, and then allowed to cool to room temperature. The solvent was removed by rotary vacuum evaporation to leave two layers. Diethylether (500 mL) was added and the mixture was stirred for 1 hr. The mixture was allowed to settle and the top layer was decanted and discarded. Additional diethylether (500 mL) was added. The mixture was stirred for 24 h, and the top layer was again decanted and discarded. The remaining oil was dried in a vacuum oven at 65° C. for 4 days to yield 67 g of product.

Example 2

Synthesis of 1,10-Bis(diallylmethylammonio)decane dibromide

To a 1 L Morton flask was added diallylmethylamine (86.1 g), 1,10-dibromodecane (112 g), and methanol (100 mL). The mixture was heated to 65° C. for 24 h, and then allowed to cool to room temperature. The solvent was removed by rotary vacuum evaporation. Diethylether (400 mL) was added and the mixture was stirred for 1 hr. The mixture was allowed to settle and the top layer was decanted and discarded. The remaining oil was dried by rotary vacuum evaporation to yield 215 g of product.

Example 3

Synthesis of 1,6-Bis(diallylmethylammonio)hexane dibromide

To a 1 L Morton flask was added diallylmethylamine (74.6 g), 1,6-dibromohexane (77 g), and methanol (100 mL).

The mixture was heated to 65° C. for 17 h, and then allowed to cool to room temperature. Diethylether (300 mL) was added and the mixture was stirred for 1 hr. The solid was collected by filtration and resuspended in diethylether (200 mL). The mixture was stirred for 1 hr, and the solid again collected by filtration. The solid was then dried in a vacuum oven at 50° C. for 3 days to yield 136 g of product.

Example 4

Synthesis of Poly[1,10-bis(diallylmethylammonio)-decane dibromide]

To a 250-mL, round bottom flask was added 1,10-bis (diallylmethylammonio) decane dibromide (20 g) and water (40 g). Azobisisobutyramidine dihydrochloride (0.5 mL of a 50% aqueous solution) was added and nitrogen was bubbled through the mixture for 1 hr. The mixture was then heated to 60° C. with stirring for 4 hr, at which time additional azobisisobutyramidine dihydrochloride (0.5 mL of a 50% aqueous solution) was added.

After 18 hr the solution was allowed to cool to room temperature. The resulting gel was removed and ground in a blender with water (500 mL). The solid was collected by centrifugation and resuspended in methanol (500 mL). After stirring for 1 hr, the solid was collected by filtration and resuspended in aqueous NaCl (500 mL of 1.5 M solution). After again stirring for 1 hr, the solid was collected by filtration. The aqueous NaCl rinse was repeated twice more, and the solid was rinsed with water until the conductivity of the rinse reached 0.3 mS/cm. The solid was dried in a forced air at 60° C. to yield 10.0 g of product.

Example 5

Synthesis of Copoly[1,10-bis (diallylmethylammonio)decane dibromide/ diallylmethyldodecylammonium bromide]

To a 500-mL round bottom flask was added 1,10-bis (diallylmethylammonio) decane dibromide (21.1 g), diallylmethyldodecylammonium bromide (21.1 g), and water (52 g). Azobisisobutyramidine dihydrochloride (1 mL of a 50% aqueous solution) was added and nitrogen was bubbled through the mixture for 1 hr. The mixture was then heated to 60° C. with stirring for 18 hr. The resulting gel was allowed to cool to room temperature. The gel was removed and ground in a blender with water (250 mL). The solid was collected by filtration and resuspended in methanol (250 mL). The solid was collected by filtration and resuspended in methanol (250 mL). After stirring for 1 hr, the solid was collected by filtration and resuspended in aqueous NaCl (250 mL of 1.5 M solution). After again stirring for 1 hr, the solid was collected by filtration. The aqueous NaCl rinse was repeated twice more, and the solid was rinsed with water until the conductivity of the rinse reached 0.08 mS/cm. The solid was dried in a forced-air oven at 60° C. to yield 17.6 g of product.

Example 6

Synthesis of Epichlorohydrin Crosslinked Poly (diallylmethylamine)

A crosslinked gel of N-methyl-N; N-diallylamine polymer was prepared by reacting the corresponding linear soluble polymer with epichlorohydrin. The starting material, poly(diallylmethylamine) was obtained in the form of its hydrochloride salt from Nitto Boseki Co. The polymer was obtained as a 60% aqueous solution (PAS-M-1, Lot # 51017). The chemical process to obtain insoluble gels of this polymer involved partial neutralization of the amine hydrochloride polymer with a base followed by treatment with a predetermined amount of epichlorohydrin at room temperature. Experimental details to obtain a typical crosslinked gel of poly(diallylmethylamine hydrochloride) are given below.

83 g of the polymer solution was diluted with 170 mL deionized water. While stirring, 6.8 g NaOH was added to the polymer solution. The reaction mixture was allowed to stir until all NaOH had dissolved. When the temperature of the solution had dropped to below 30° C., epichlorohydrin (1.2 mL) was added and stirring continued. The reaction medium slowly became viscous and after about 80 minutes, had gelled and the stirring was stopped. The polymer gel was left at room temperature for an additional 60 hr. The polymer slab was broken into smaller pieces and dispersed in 400 mL deionized water. The resulting suspension was stirred for 2 hr and then filtered. The swollen polymer particles were resuspended in 600 mL deionized water, stirred for 45 minutes and collected by filtration. The process was repeated with 800 mL water and 1 hr stirring. After filtration, the filtrate showed a conductivity of 4 mS/cm. The filtered polymer (swollen gel) was dried in a forced air oven at 60° C. to yield 42 g of product.

Example 7

Alkylation of Crosslinked Poly(diallylmethylamine) with 1-bromodecane 25 g of the ground polymer (Example 7) taken in a 1 liter 3-necked round bottom flask was suspended in 250 mL deionized water. The polymer swelled significantly and was stirred with a mechanical stirrer. To this swollen gel was added 100 g 1-bromodecane dissolved in 250 mL ethanol and the reaction mixture was stirred for 10 minutes. Subsequently, 5 g of 50% aqueous sodium hydroxide was added and the reaction mixture was stirred at room temperature for 40 minutes followed by heating to 75° C. for 1 hr. 2 g NaOH solution was then added followed by additional 2 g of NaOH solution after another 1.5 hr (the base addition was such as to maintain the pH between 10 and 12). The reaction mixture was stirred at 75° C. for an additional 18 hours, after which time heating was discontinued. After cooling to 30° C., 5 mL concentrated HCl was added and stirring was continued for 30 minutes. The pH of the medium dropped to 1.8. The polymer was filtered and washed with 500 mL deionized water followed by 500 mL methanol. Polymer particles were suspended in 600 mL methanol and stirred for 40 minutes. After removing the solvent by filtration, the polymer was suspended in 500 mL of 2 M NaCl solution and stirred for 40 minutes. The polymer was filtered and this process of NaCl treatment was repeated two more times. The filtered polymer cake was washed with 500 mL deionized water and suspended in 500 mL deionized water. After stirring for 30 minutes the polymer was filtered and resuspended in 700 mL deionized water and stirred for 30 minutes. Concentrated HCl (2 mL) was added to the suspension and the mixture was stirred for 15 minutes. The pH of the suspension was found to be 2.25. After stirring for an additional 20 minutes, the polymer was filtered and dried at 60° C. in a forced air oven, yielding 54.6 g of the alkylated polymer as a light yellow solid. The polymer was ground and passed through a 140 mesh sieve.

Example 8

Alkylation of Crosslinked poly(diallylmethylamine) with 1-bromododecane 10 g of the ground polymer (Example 6) was suspended in 100 mL deionized water in a 500 mL 3-necked round-bottomed flask. The polymer swelled significantly and was stirred with a mechanical stirrer. To this swollen gel, 28 g 1-bromodecane dissolved in 100 mL ethanol was added and the reaction mixture was stirred for 10 minutes. 2 g of 50% aqueous sodium hydroxide was then added and the reaction mixture was stirred at room temperature for 40 minutes, followed by heating to 75° C. for 1 hr. 1 g NaOH solution was then added followed by an additional 1 g of NaOH solution after another 1.5 hr (the base addition was such as to maintain the pH between 10 and 12). The reaction mixture was stirred at 75° C. for an additional 18 h after which time the heating discontinued. After cooling to 30° C., concentrated HCl (2 mL) was added and the mixture was stirred for 30 minutes. The polymer was filtered and washed with 500 mL deionized water followed by 500 mL methanol. Polymer particles were suspended in 300 mL methanol and stirred for 40 minutes. After removing the solvent by filtration, the polymer was suspended in 500 mL 2M NaCl solution and stirred for 40 minutes. It was filtered and this process of NaCl treatment was repeated two more times. The filtered polymer cake was washed with 500 mL deionized water and suspended in 500 mL deionized water. After stirring for 30 minutes the polymer was filtered and resuspended in 500 mL deionized water and stirred for 30 minutes. Concentrated HCl (2 mL) was added to the suspension and the mixture was stirred for 15 minutes. The pH of the suspension was found to be 2.2. After stirring for an additional 20 minutes, the polymer was filtered and dried at 60° C. in a forced air oven, yielding 18 g of the alkylated polymer as a pale white solid. The polymer was ground and passed through a 140 mesh sieve.

Example 9

Preparation of (3-chloropropyl)-dodecyldimethylammonium bromide

A two-liter, 3-necked, round-bottomed flask equipped with an air condenser and a magnetic stirring plate was charged with N,N-dimethyldodecylamine (297.24 grams, 1.40 moles), 1-bromo-3-chloropropane (220.44 grams, 1.40 moles) and methanol (250 mL). Reaction was maintained at 65° C. for 24 hours. Methanol was removed by rotary evaporation under reduced pressure to yield a brown sludge. To the sludge was added methyl-tert-butylether (2 liters) causing a white solid to form. The mixture was stirred for two hours and a semi-crystalline, white particulate was collected by vacuum filtration. The particulate was dried in a vacuum oven at 35° C. for 24 hours. Yield 228.2 grams (0.61 moles, 44%).

(4-Chlorobutyl)dodecyldimethylammonium bromide and (6-chlorohexyl)dodecyldimethylammonium bromide can be prepared by a similar process using the appropriate bromochloroalkane and dodecyldimethylamine.

Example 10

Alkylation of Crosslinked Poly(diallylmethylamine) with (3-chloropropyl) dimethyldodecylammonium bromide A mixture of 11 g crosslinked polymer gel (Example 6) and 74 g (3-chloropropyl)-dimethyldodecylammonium bromide was dispersed in 250 mL deionized water and heated to 75° C. with stirring. After stirring at 75° C. for 15 minutes, 2 g of a 50% aqueous NaOH solution was added to the reaction mixture. After 2 hr, 1 g of NaOH solution was added followed by an additional 1 g after another 1 hr and the mixture was stirred at 75° C. for 23 hr. The reaction mixture was then allowed to cool. After cooling to 30° C., 3 mL concentrated HCl was added and the mixture was stirred for 30 minutes. The polymer was filtered and washed with 200 mL methanol. The filtered polymer particles were dispersed in 400 mL methanol and stirred for 45 minutes and filtered. This process was repeated one more time, then the filtered polymer was suspended in 500 mL 2M NaCl solution, stirred for 45 minutes and filtered. This process of NaCl treatment was repeated twice and the filtered polymer was suspended in 500 mL deionized water. The mixture was stirred for 45 minutes, filtered, resuspended in 400 mL deionized water and stirred for an additional 40 minutes. To this suspension, 1 mL concentrated HCl was added and the mixture was stirred for 20 minutes. The polymer was filtered and dried in a forced air oven at 60° C., yielding 29 g of alkylated polymer as a light yellow solid which was ground and passed through a 140 mesh sieve.

Example 11

Alkylation of Crosslinked Poly(diallylmethylamine) with (4-chlorobutyl)-dimethyldodecylammonium bromide A mixture of 10 g 3% crosslinked polymer gel (Example 6) and 76 g (4-chlorobutyl)dimethyldodecylammonium bromide was dispersed in 250 mL deionized water and heated to 70° C. with stirring for 15 minutes. 2 g 50% aqueous solution of NaOH was then added to the reaction mixture. After 2 hr, 1 g NaOH solution was added followed by additional 1 g after another 2 hr. The reaction mixture was then stirred at 70° C. for 20 hours. 1 g NaOH was then added and the reaction mixture was kept at 70° C. After 20 hr heating, 1 g NaOH solution was added and the reaction mixture was kept at 70° C. with stirring for 2 hr. After cooling to 30° C., 2 mL of concentrated HCl was added and the mixture was stirred for 20 minutes. The polymer was filtered and washed successively with 200 mL deionized water and 200 mL methanol. The filtered polymer particles were then dispersed in 500 mL methanol, stirred for 30 minutes, and filtered. This process was repeated an additional time and the filtered polymer was suspended in 400 mL 2M NaCl solution, stirred for 45 minutes and filtered. After repeating NaCl treatment twice, the filtered polymer was suspended in 400 mL deionized water. The mixture was stirred for 30 minutes, filtered, resuspended in 400 mL deionized water and stirred for an additional 40 minutes. To this polymer suspension, 1 mL concentrated. HCl was added and the mixture was stirred for 20 minutes. The polymer was then filtered and dried in a forced air oven at 60° C., yielding 27 g alkylated polymer as a light yellow solid which was ground and passed through a 140 mesh sieve.

Example 12

Alkylation of Crosslinked Poly(diallylmethylamine) with (6-chlorohexyl)-dimethyloctylammonium bromide

A mixture of 10 g 3% crosslinked polymer gel (Example 6) and 71 g (6-chlorohexyl)dimethyldodecylammonium bromide was dispersed in 200 mL deionized water and heated to 75° C. with stirring for 15 minutes. 2 g 50% aqueous solution of NaOH was then added to the reaction mixture. After 3 hr, 1 g NaOH solution was added. After 2.5 hr an additional 1 g of NaOH solution was added and the reaction mixture was stirred at 75° C. for 22 hr. 0.5 g NaOH was then added and heating was continued for an additional 2 hr. After cooling to 30° C., 2 mL concentrated HCl was added and the mixture was stirred for 15 minutes. The polymer was then filtered and washed successively with 200 mL deionized water and 200 mL methanol. The filtered polymer particles were then dispersed in 500 mL methanol, stirred for 30 minutes and filtered. This process was repeated two times, then the filtered polymer was suspended in 400 mL 2M NaCl solution, stirred for 45 minutes and filtered. After repeating the NaCl treatment twice, the filtered polymer was suspended in 400 mL deionized water. The mixture was stirred for 30 minutes, filtered, and resuspended in 400 mL deionized water and stirred for an additional 40 minutes. To this polymer suspension was added 1 mL concentrated HCl and the mixture was stirred for 20 minutes. The polymer was filtered and dried in a forced air oven at 60° C., yielding 25 g alkylated polymer as a white solid, which was ground and passed through a 140 mesh sieve.

Example 13

Alkylation of Crosslinked Poly(diallylmethylamine) with 1-bromodecane

This example illustrates alkylation of the 4.5% crosslinked poly(diallylmethylamine) with different amounts of 1-bromodecane to obtain quaternized polyamines bearing varying amounts of hydrophobic groups. For this purpose, the polymer was treated with varying mole fractions of 1-bromodecane (1.0, 0.75, 0.50, 0.25 and 0.10). Table 1 summarizes amounts of 1-bromoalkane used to obtain polymers of varying degree of alkylation and the yield of alkylated polymer per gram of the 4.5 % crosslinked poly (diallylmethylamine) (Example 2). This g/g yield is a measure of the degree of alkylation of the polymer.

10 g of the 4.5% crosslinked poly(diallylmethylamine) was suspended in 150 mL deionized water. While stirring, 2 g 50% aqueous NaOH solution was added to the polymer and the suspension was stirred for 15 minutes. At this time an ethanol solution of 1-bromodecane (2.5 mL ethanol/g 1-bromodecane) was added and the reaction mixture was heated to 75° C. with stirring. After 2 hr, 1 g NaOH was added, followed by an additional 1 g of NaOH after another 2 hr. The reaction mixture was stirred at 75° C. for 18 hours and was then allowed to cool. After cooling to 30° C., 2 mL concentrated HCl was added and the mixture was stirred for 15 minutes. The polymer was filtered and washed with 200 mL deionized water and 200 mL methanol for 30 minutes and filtered. This process was repeated twice and the filtered polymer was suspended in 400 mL of 2M NaCl solution, stirred for 45 minutes and filtered. After repeating the NaCl treatment twice, the filtered polymer was suspended in 400 mL deionized water. The mixture was stirred for an additional 30 minutes, filtered, resuspended in 400 mL deionized water and stirred for an additional 40 minutes. To this polymer suspension was added 1 mL concentrated HCl and the mixture was stirred for 20 minutes. The polymer was filtered, dried in a forced air oven at 60° C., ground and passed through a 140 mesh sieve. Yield of the polymers for different amounts of the 1-bromodecane used are summarized in Table 1. The calculation of % alkylation assumed protonation of 50% of the amino nitrogen atoms.

TABLE 1

Results of the alkylation of 4.5% crosslinked poly(diallylmethylamine) with varying amounts of 1-bromodecane ($C_{10}H_{21}Br$) ("ratio" = ratio of 1-bromodecane to polymer amino groups (mole/mole)).

| Polymer Used (g) | $C_{10}H_{21}Br$ used (g) | Ratio | product yield (g) | product/ starting polymer (g/g) | % alkylation |
|---|---|---|---|---|---|
| 10.0 | 17.0 | 1.0 | 17 | 1.7 | 35 |
| 10.0 | 12.5 | 0.75 | 16.8 | 1.68 | 34 |
| 10.0 | 8.0 | 0.50 | 14.3 | 1.43 | 22 |
| 10.0 | 4.25 | 0.25 | 11.8 | 1.18 | 9 |
| 10.0 | 1.70 | 0.10 | 10.6 | 1.06 | 3 |

Example 14

Alkylation of Crosslinked Poly(diallylmethylamine) with 1-bromo-tetradecane

10 g of 4.5% crosslinked polydiallylmethylamine (Example 6) was suspended in 100 mL in a 500 mL 3-necked round-bottomed flask of deionized water. The polymer swelled significantly and was stirred with a mechanical stirrer. To this swollen gel, was added 32 g 1-bromotetradecane dissolved in 100 mL ethanol, and the reaction mixture was stirred for 10 minutes. 2 g 50% aqueous sodium hydroxide was then added and the reaction mixture was stirred at room temperature for 40 minutes followed by heating to 75° C. for 1 hr. 1 g NaOH solution was then added followed by an additional 1 g of NaOH solution after another 1.5 hr (the base addition was such as to maintain the pH between 10 to 12). The reaction mixture was stirred at 75° C. for an additional 18 hours after which time the heating was discontinued. After cooling to 30° C., 2 mL concentrated HCl was added and the mixture was stirred for 30 minutes. The polymer was filtered and washed with 500 mL deionized water followed by 500 mL methanol. Polymer particles were suspended in 300 mL methanol and stirred for 40 minutes. After removing the solvent by filtration, the polymer was suspended in 500 mL of 2M NaCl solution and stirred for an additional 40 minutes. The polymer was filtered and this process of NaCl treatment was repeated twice. The filtered polymer cake was then washed with 500 mL deionized water and suspended in 500 mL deionized water. After stirring for 30 minutes the polymer was filtered and resuspended in 500 mL deionized water and the suspension was stirred for 30 minutes. 1 mL concentrated HCl was then added to the suspension, which was stirred for another 55 minutes. The polymer was then filtered and dried at 60° C. in a forced air oven, yielding 22 g of the alkylated polymer. The polymer was ground and passed through a 140 mesh sieve.

Example 15

Alkylation of Crosslinked Poly(diallylmethylamine) with 1-Bromooctane

10 g of 4.5% crosslinked poly(diallylmethylamine) (Example 7) was suspended in 100 mL in a 500 mL 3-necked round bottom flask of deionized water. The polymer swelled significantly and was stirred with a mechanical stirrer. To this swollen gel, was added 23 g 1-bromooctane dissolved in 100 mL ethanol and the reaction mixture was stirred for 10 minutes. 2 g of 50% aqueous sodium hydroxide was then added and the reaction mixture was stirred at room temperature for 40 minutes, followed by heating to 75° C. for 1 hr. 1 g NaOH solution was then added, followed by an additional 1 g of NaOH solution after another 1.5 hr. The reaction mixture was allowed to stir at 75° C. for an additional 18 hours after which time the heating was discontinued. After cooling to 30° C., 2 mL concentrated HCl was added and stirring was continued for 30 minutes. The polymer was filtered and washed with 500 mL deionized water followed by 500 mL methanol. Polymer particles were suspended in 300 mL methanol and stirred for 40 minutes. After removing the solvent by filtration, the polymer was suspended in 500 mL 2M NaCl solution and the suspension was stirred for 40 minutes. The polymer was filtered and this process of NaCl treatment was repeated twice. The filtered polymer cake was washed with 500 mL deionized water and suspended in 500 mL deionized water. After stirring for 30 minutes the polymer was filtered, resuspended in 500 mL deionized water, and stirred for 30 minutes. 1 mL concentrated HCl was added to the suspension and stirred for 35 minutes. The polymer was then filtered and dried at 60° C. in a forced air oven, yielding 15.8 g of the alkylated polymer. The polymer was ground and passed through a 140 mesh sieve.

Example 16

Alkylation of Crosslinked Poly(diallylmethylamine) with 1-Bromohexane 10 g of 4.5% crosslinked poly(diallylmethylamine) (Example 6) taken in a 500 mL 3-necked round bottom flask was suspended in 100 mL deionized water. The polymer swelled significantly and was stirred with a mechanical stirrer. To this swollen gel was added, 19 g 1-bromodecane dissolved in 100 mL ethanol was added and the reaction mixture was stirred for 10 minutes. 2 g of 50% aqueous sodium hydroxide was then added and the reaction mixture was stirred at room temperature for 40 minutes, followed by heating to 75° C. for 1 hr. 1 g NaOH solution was then added followed by an additional 1 g of NaOH solution after another 1.5 hr. The reaction mixture was stirred at 75° C. for an additional 18 hours after which time the heating was discontinued. After cooling to 30° C., 2 mL concentrated HCl was added and the mixture was stirred for 30 minutes. The pH of the medium at this point was 2.0. The polymer was filtered and washed with 500 mL deionized water followed by 500 mL methanol. The polymer particles were suspended in 300 mL methanol and stirred for 40 minutes. After removing the solvent by filtration, the polymer was suspended in 500 mL of 2 M NaCl solution and the suspension was stirred for 40 minutes. The polymer was filtered and this process of NaCl treatment was repeated twice. The filtered polymer cake was washed with 500 mL deionized water and suspended in 500 mL deionized water. After stirring for 30 minutes, the polymer was filtered, resuspended in 500 mL deionized water and stirred for 30 minutes. 1 mL concentrated HCl was added to the suspension, which was stirred for 35 minutes. The polymer was then filtered and dried at 60° C. in a forced air oven, yielding 13.7 g of the alkylated polymer. The polymer was ground and passed through a 140 mesh sieve.

Example 17

Synthesis of Quaternized N-alkyl diallylmethylammonium Salts

Synthesis of N-decyldiallylmethylammonium bromide.

Diallylmethylamine (33.3 g) and 1-bromodecane (66.6 g) were dissolved in 100 mL methanol and the reaction mixture was stirred at 65° C. for 48 hours. After cooling to room temperature, the methanol was removed under reduced pressure. The residual viscous oil was precipitated into 800 mL dry ether with rapid stirring. The ether layer was decanted and the residue was again treated with 500 mL dry ether. After stirring for 15 minutes the solvent was removed and the oily residue was dried under vacuum at 35° C. for 48 hours, yielding 78 g of the product.

Synthesis of N-(N,N-dimethyl-N-dodecylammonio) propyldiallylmethylammonium chloride bromide A mixture of 22 g diallylmethylamine and 74 g 3-chloropropyldodecyldimethylammonium bromide were dissolved in 100 mL methanol and the reaction mixture was stirred at 65° C. for 48 hours. The progress of the reaction was monitored by the disappearance of the diallllymethylamine by thin layer chromatography (TLC). After cooling to room temperature, the solvent was removed under reduced pressure. The residual viscous oil was precipitated into 800 mL dry ether with rapid stirring. The ether layer was decanted and the residue was again treated with 500 mL dry ether. After stirring for 15 minutes the solvent was removed and the oily residue was dried under vacuum at 35° C. for 48 hours, yielding 70 g of the product.

Synthesis of N-(N,N-dimethyl-N-dodecylammonio)butyl-diallylmethylammonium chloride bromide.

A mixture of 22 g diallylmethylamine and 75 g 4-chlorobutyldimethyldodecylammonium bromide were dissolved in 100 mL methanol and the reaction mixture was stirred at 65° C. for 48 hours. The progress of the reaction was monitored by the disappearance of the diallylmethylamine by thin layer chromatography (TLC). After cooling to room temperature, the solvent was removed under reduced pressure. The residual viscous oil was precipitated into 800 mL dry ether with rapid stirring. The ether layer was decanted and the residue was again treated with 500 mL dry ether. After stirring for 15 minutes the solvent was removed and the oily residue was dried under vacuum at 35° C. for 48 hours, yielding 65 g of the product.

Synthesis of poly(N-decyldiallylmethylammonium bromide) crosslinked with methylenebis(acrylamide)

25 g N-decyldiallylmethylammonium bromide, 3 g N,N-methylenebisacrylamide and 300 mg 2,2"-azobis(2-amidinopropane)dihydrochloride were dissolved in 100 mL deionized water. The solution was bubbled with a slow stream of nitrogen for 30 minutes then heated to 70° C. with stirring. After 2 hr, the reaction mixture turned cloudy with formation of a suspension. The mixture was kept at 70° C. for a period of 18 hours and then allowed to cool. The suspension was centrifuged. The residue dispersed in 200 mL deionized water, stirred for 30 minutes and centrifuged. After removal of the supernatant, the residue was suspended in 200 mL methanol, stirred for 30 minutes and centrifuged. The residue was suspended in 300 mL methanol and the suspension was refluxed for 1 hr. After cooling to room temperature, the suspension was filtered and the white solid was dried at 60° C. for 24 hr to yield 10 g of the polymer. The polymer was ground and passed through 140 mesh sieve.

Example 19

Synthesis of Crosslinked Poly(diallylammonium chloride-co-sulfur dioxide) Copolymer 111 g of a 20% solution of copoly (diallylmethylammonium chloride-co-sulfur dioxide) (PAS-92, obtained from Nitto Boseki Co., Japan) was treated with 2.2 g solid NaOH with stirring. The solution turned cloudy and phase separation occurred. The bottom viscous layer was separated from the top layer and the former was diluted with 20 mL water. To this solution, 0.6 mL epichlorohydrin was added and the reaction mixture was allowed to stir for 2 hr. The reaction medium slowly became increasingly viscous and was left at room temperature for 48 hours, during which period it turned into a gel. The resulting polymer gel was broken into smaller pieces and was dispersed in 1 liter deionized water. The suspension was stirred for 1 hr and filtered. The swollen polymer particles were resuspended in 800 mL deionized water and stirred for 1.5 hr. The polymer particles were then filtered and dried in a forced air oven at 60° C. to yield 16 g of polymer. The dried polymer was ground and passed through a 10 mesh sieve.

Example 20

Alkylation of 6% Crosslinked Copoly (diallylmethylamine-co-sulfur dioxide) with 1-bromodecane The polymer (5 g) of Example 20 was placed in a 500 mL 3-necked round bottom flask and suspended in 100 mL deionized water. The polymer swelled significantly and was stirred with a mechanical stirrer. To this swollen gel, a solution of 18 g 1-bromodecane in 100 mL ethanol was added and the reaction mixture stirred for 10 minutes. Subsequently, 2 g 50% aqueous sodium hydroxide was added and the reaction mixture was stirred at room temperature for 30 minutes followed by heating to 75° C. After 1 hr, 0.5 g NaOH solution was added followed by an additional 0.5 g of NaOH solution after another 1.5 hr. The reaction mixture was allowed to stir at 75° C. for an additional 18 hr after which time the heating was discontinued. After cooling to 30° C., 2 mL concentrated HCl was added and the mixture was stirred for 30 minutes. The pH of the medium dropped to 1.2. The polymer was filtered off and washed with 500 mL deionized water and 500 mL methanol. Polymer particles were suspended in 300 mL methanol and stirred for 40 minutes. After removing the solvent by filtration, the polymer was suspended in 500 mL 2M NaCl solution and stirred for 40 minutes. The suspension was filtered and the NaCl treatment was repeated two more times. The filtered polymer cake was washed with 500 mL deionized water and suspended in 500 mL deionized water. After stirring for 30 minutes it was filtered and resuspended in 500 mL deionized water and stirred for 30 minutes. 1 mL of concentrated HCl was added to the suspension and the suspension was stirred for 35 minutes. The polymer was then filtered and dried at 60° C. in a forced air oven, yielding 9.1 g of the alkylated polymer. The polymer was ground and passed through a 140 mesh sieve.

Example 21

Alkylation of Crosslinked Copoly (diallylmethylamine-co-sulfur dioxide) with (3-chloropropyl)-dimethyldodecylammonium bromide To a mixture of 5 g of the polymer of Example 20 and 30 g (3-chloropropyl)dimethyldodecylammonium bromide in a 500 mL 3-necked round bottom flask was added 150 mL deionized water. The resulting mixture was stirred with a mechanical stirrer. 2 g of 50% aqueous sodium hydroxide was added and the reaction mixture was stirred at room temperature for 30 minutes, followed by heating to 75° C. for 1 hr. NaOH solution (0.5 g) was added, followed by an additional 0.5 g of NaOH solution after another 1.5 hr. he reaction mixture was allowed to stir at 75° C. for an additional 18 hr after which time the heating was discontinued. After cooling to 30° C., 2 mL concentrated HCl was added and the mixture was stirred for 30 minutes. The pH of the medium dropped to 2.8. The polymer was filtered off and washed with 500 mL deionized water and 500 mL methanol. Polymer particles were then suspended in 300 mL methanol and the suspension was stirred for 40 minutes. The polymer was isolated by filtration and then suspended in 500 mL 2M NaCl solution. The suspension was stirred for 40 minutes. The polymer was filtered off and this NaCl treatment was repeated two more times. The filtered polymer cake was washed with 500 mL deionized water and then suspended in 500 mL deionized water. After stirring for 30 minutes the polymer was filtered off and resuspended in 500 mL deionized water. The suspension was stirred for 30 minutes. 1 mL concentrated HCl was added to the suspension and the suspension was stirred for 35 minutes. The polymer was then filtered and dried at 60° C. in a forced air oven, yielding 11.4 g of the alkylated polymer. The polymer was ground and passed through a 140 mesh sieve.

Example 22

Preparation of Poly(diallylammonium chloride)

100 g diallylamine and 100 mL deionized water were placed in a 1 liter beaker and the mixture was allowed to stir. To this stirred mixture, 37% aqueous HCl was added slowly with concurrent measurement of pH. When the pH of the solution dropped below 7, addition of acid stopped. The solution was extracted with 600 mL diethyl ether. To the aqueous solution, 3 g 2,2'-azobis(2-amidinopropane) dihydrochloride was added and the solution was bubbled with nitrogen gas for 45 minutes. The solution was then heated to 70° C. for 48 hr, after which time the reaction mixture has turned viscous. Heating was discontinued and, after cooling to room temperature, 315 g of polymer solution was obtained.

Example 23

Synthesis of insoluble crosslinked polydiallylamine

The polydiallylammonium chloride solution of Example 23 (150 g) was diluted with 50 mL deionized water. Solid NaOH (6.75 g) was added to the polymer solution with stirring. The reaction mixture was stirred until the NaOH has dissolved and temperature of the solution had dropped to below 30° C. To this partially neutralized polymer solution, epichlorohydrin (1.2 mL) was added and stirring was continued. The reaction medium slowly became increasingly viscous and after about 50 minutes it gelled and the stirring stopped. This gelled polymer was left at room temperature for an additional 48 hr to yield a semi-brittle polymer slab. The polymer slab was broken into smaller pieces and was dispersed in 1 L deionized water. The resulting suspension was stirred for 1.5 hr and then filtered. The swollen polymer particles were resuspended in 1 L deionized water and the suspension was stirred for 40 minutes. The polymer particles were filtered off and dried in a forced air oven at 60° C. to yield 56 g of pale white solid polymer. The dried polymer was ground and passed through a 10 mesh sieve.

Example 24

Alkylation of Crosslinked Polydiallylamine with 1-bromododecane

The ground polymer of Example 23 (5 g) was placed in a 500 mL 3-necked round-bottomed flask and suspended in 100 L deionized water and the suspension was stirred with a mechanical stirrer. To this swollen gel, a solution of 15 g 1-bromodecane in 100 mL ethanol was added and the reaction mixture was stirred for 10 minutes. 2 g 50% aqueous sodium hydroxide was then added and the reaction mixture was stirred at room temperature for 40 minutes followed by heating to 75° C. Subsequently, an additional 4 g 50% NaOH was added in a 1 g batch at an interval of 1.5 hr (the base addition maintained a pH between 10 to 12). The reaction mixture was allowed to stir at 75° C. for a total period of 20 hr. After cooling to 30° C., 2 mL concentrated HCl was added and the mixture was stirred for 30 minutes. The polymer was filtered off and washed with 500 mL deionized water and 500 mL methanol. The filtered polymer particles were slurried in methanol (400 mL), stirred for 40 minutes and reisolated by filtration. This process was then repeated. The polymer was suspended in 500 mL 2M NaCl solution and the suspension was stirred for 40 minutes. The polymer was filtered off and this NaCl treatment was repeated two more times. The fitered polymer cake was washed with 500 mL deionized water and suspended in 500 mL deionized water. After stirring the suspension for 30 minutes, the polymer was filtered off and resuspended in 500 mL deionized water. The resulting suspension was stirred for 30 minutes. 1 mL concentrated HCl was added to the suspension, which was then stirred for 35 minutes. The pH of the suspension was found to be 2.2. The polymer was then filtered off and dried at 60° C. in a forced air oven, yielding 13.3 g of the alkylated polymer as a pale white solid. The polymer was ground and passed through a 140 mesh sieve.

Example 25

Alkylation of Crosslinked Polydiallylamine with (3-chloropropyl)dimethyldodecylammonium bromide

A mixture of 5 g of the crosslinked polymer gel of Example 23 and 28 g (3-chloropropyl)dimethyldodecylammonium bromide was dispersed in 150 mL deionized water and the suspension was stirred. To this suspension 2 g 50% NaOH was added and the mixture was stirred for 15 minutes. The mixture was then heated with stirring to 75° C. An additional 4 g 50% NaOH was added in 1 g batches at 1.5 hr intervals (the base addition was such as to maintain the pH between 10 to 12). After stirring at 75° C. for a total period of 18 hr, the reaction mixture was allowed to cool. After cooling to 30° C., 2 mL concentrated HCl was added and the mixture was stirred for 30 minutes. The polymer particles were filtered off and washed with 200 mL methanol. The filtered polymer particles were suspended twice in methanol (400 mL) and the suspension was stirred for 40 minutes. This process was repeated. After removing the polymer by filtration, the polymer was suspended in 500 mL 2M NaCl solution and the suspension was stirred for 40 minutes. This NaCl treatment was repeated twice and the filtered polymer was suspended in 500 mL deionized waer. The mixture was stirred for an additional 45 minutes, filtered, resuspended in 400 mL deionized water and stirred for another 40 minutes. To this suspension, 1 mL concentrated HCl was added and the mixture was stirred for 20 minutes. The polymer was filtered off and dried in a orced air oven at 60° C., yielding 13.2 g of alkylated olymer as a light yellow solid which was ground and passed through a 140 mesh sieve.

Example 26

Alkylation of Crosslinked Poly(diallylmethylamine) with 1-bromooctane

The 3% crosslinked poly(diallylmethylamine) of Example 6 (5 g) was taken in a 500 mL 3-necked round-bottomed flask and suspended in 110 mL deionized water. The polymer swelled significantly and was stirred with a mechanical stirrer. To this swollen gel, a solution of 11.1 g 1-bromooctane in 50 mL ethanol was added and the reaction mixture was stirred for 10 minutes. 1 g 50% aqueous sodium hydroxide was then added and the reaction mixture was stirred at room temperature for 40 minutes followed by heating to 75° C. for 1.5 hr. 1 g NaOH solution was added, and the reaction mixture was allowed to stir at 75° C. for an additional 18 hr. After the mixture had cooled to 30° C., 2.5 mL concentrated HCl was added and the mixture was stirred for 30 minutes. The polymer was filtered and washed with 300 mL deionized water and 300 mL methanol. Polymer particles were suspended in 300 mL methanol and the suspension was stirred for 40 minutes. After removing the polymer by filtration, the polymer was suspended in 300 mL 2 M NaCl solution and the suspension was stirred for 40 minutes. The polymer was filtered off and this NaCl treatment was repeated two more times. The filtered polymer cake was washed with 400 mL deionized water, then suspended in 400 mL deionized water. After the suspension as stirred for 30 minutes, it was filtered and the polymer as resuspended in 400 mL deionized water and this uspension was stirred for an additional 30 minutes. 1 mL concentrated HCl was added to the suspension, which was then stirred for 30 minutes. The polymer was filtered and dried at 60° C. in a forced air oven, yielding 7.0 g of the alkylated polymer as a pale white solid. The polymer was ground and passed through a 140 mesh sieve.

Example 27

Alkylation of Crosslinked Poly(diallylmethylamine) with 1-bromotetradecane

The 3% crosslinked poly(diallylmethylamine) of Example 6 (5 g) was taken in a 500 mL 3-necked round bottomed flask and suspended in 100 mL deionized water. The polymer swelled significantly and was stirred with a mechanical stirrer. To this swollen gel, 16 g 1-bromotetradecane dissolved in 40 mL ethanol was added and the reaction mixture was stirred for 10 minutes. 1 g 50% aqueous sodium hydroxide was then added and the reaction mixture was stirred at room temperature for 40 minutes followed by heating to 75° C. for 1.5 hr. 1 g NaOH solution was then added and the reaction mixture was stirred at 75° C. for additional 18 hr. After cooling to 30° C., 2.5 mL concentrated HCl was added and the mixture was stirred for 30 minutes. The polymer was filtered and washed with 300 mL deionized water and 300 mL methanol. Polymer particles were suspended in 300 mL methanol and the suspension was stirred for 40 minutes. After removing the polymer by filtration, the polymer was suspended in 300 mL 2M NaCl solution and the suspension was stirred for 40 minutes. The polymer was filtered off and this NaCl treatment was repeated two more times. The filtered polymer cake was washed with 400 mL deionized water and suspended in 400 mL deionized water. After stirring for 30 minutes the suspension was filtered and the polymer was resuspended in 400 mL deionized water. This suspension was stirred for an additional 30 minutes. 1 mL concentrated HCl was then added to the suspension and stirring continued for 30 minutes. The polymer was filtered off and dried at 60° C. in a forced air oven, yielding 9.0 g of the alkylated polymer as a pale white solid. The polymer was ground and passed through a 140 mesh sieve.

Example 28

Alkylation of Crosslinked Poly(diallylmethylamine) with (3-chloropropyl)dimethyloctadecylammonium bromide (3-Chloropropyl)dimethyloctadecylammonium bromide was prepared by the general method of Example 10 starting with dimethyloctadecylamine. A mixture of the crosslinked polymer gel of Example 1 and 35 g (3-chloropropyl) dimethyloctadecylammonium bromide was dispersed in 150 mL deionized water and the mixture was heated to 70° C. with stirring for 15 minutes. 2 g 50% aqueous solution of NaOH and 50 mL ethanol were then added to the reaction mixture. After 2 hr, 0.5 g NaOH solution was added and the reaction mixture was stirred at 70° C. for 20 hr. When the reaction mixture had cooled to 30° C., 2 mL concentrated HCl was added and the mixture was stirred for another 20 minutes. The polymer was filtered off and washed with 200 mL deionized water and 200 mL methanol. The filtered polymer particles were dispersed in 500 mL methanol, stirred for another 30 minutes and then filtered. This process was repeated one more time and the filtered polymer was suspended in 300 mL 2M NaCl solution. The resulting suspension was stirred for another 45 minutes and filtered. After repeating the NaCl treatment twice, the filtered polymer was suspended in 400 mL deionized water. The mixture was stirred for 30 minutes, filtered, and the polymer was resuspended in 400 mL deionized water. The suspension was stirred for an additional 40 minutes. To this suspension was added 1 mL concentrated HCl and the mixture was stirred for 20 minutes. The polymer was filtered and dried in a forced air oven at 60° C., yielding 10.7 g alkylated polymer as a pale white solid which was ground and passed through a 140 mesh sieve.

Example 29

Alkylation of Crosslinked Poly(diallylmethylamine) with (3-Chloropropyl) dodecylpyrrolidiniumammonium bromide
Synthesis of (3-chloropropyl)dodecylpyrrolidinium bromide 47 g pyrrolidine, 149.5 g 1-bromododecane and 83 g potassium carbonate were added to 560 mL acetone. The reaction mixture was heated at 55° C. for 24 hr, then filtered. Solvent was removed from the filtrate, yielding 92 g N-dodecylpyrrolidine. 80 g N-dodecylpyrrolidine and 52.6 g 1-bromo-3-chloropropane were dissolved in 133 mL methanol and the reaction mixture was heated at 65° C. for 18 hr. After cooling to room temperature, methanol was removed under reduced pressure. The residue was poured into 2 L diethylether with stirring and the mixture was allowed to stand for another 6 hr. The white precipitate thus formed was filtered and was dried at 40° C. under a vacuum for 24 hr yielding 85 g (3-chloropropyl)dodecylpyrrolidinium bromide as a white solid, Alkylation of crosslinked poly(diallylmethylamine) with (3-chloropropyl) dodecylpyrrolidinium bromide The 3% crosslinked poly(diallylmethylamine) of Example 7 (5 g) and 30 g (3-chloropropyl) dodecylpyrrolidinium bromide were dispersed in 150 mL deionized water and the mixture was heated to 70° C. with stirring. After stirring at 70° C. for 15 minutes, 2 g 50% aqueous NaOH solution was added to the reaction mixture. After 2 hr, 1 g NaOH solution was added and the reaction mixture was allowed to stir at 70° C. for 20 hr. The reaction mixture was then allowed to cool to 30° C. 2 mL concentrated HCl was then added and the mixture was stirred for 20 minutes. The polymer was filtered off and washed with 200 mL deionized water and 200 mL methanol. The polymer particles were dispersed in 500 mL methanol and the suspension was stirred for 30 minutes and then filtered. This process was repeated one more time and the filtered polymer was suspended in 300 mL 2M NaCl solution. The resulting suspension was stirred for 45 minutes and filtered. After repeating this NaCl treatment twice, the filtered polymer was suspended in 400 mL deionized water. The mixture was stirred for 30 minutes, filtered, resuspended in 400 mL deionized water and stirred for an additional 40 minutes. To this polymer suspension was added 1 mL concentrated HCl and stirring continued for an additional 20 minutes. The polymer was filtered off and dried in a forced air oven at 60° C., yielding 13 g alkylated polymer as a pale white solid which was ground and passed through a 140 mesh sieve.

Example 30

Alkylation of Crosslinked Poly(diallylmethylamine) with (3-Chloropropyl) dodecylpiperidinium bromide
Synthesis of (3-chloropropyl)decylpiperidinium bromide N-decylpiperidine was synthesized by reacting 45.7 g iperidine with 118.7 g 1-bromodecane in 237 mL acetone in the presence of 74 g potassium carbonate. After refluxing this reaction mixture at 55° C. for 24 hr, it was filtered and acetone was removed from the filtrate to yield 61 g N-decylpiperidine. 5 g N-decylpiperidine and 42 g 1-bromo-3-chloropropane were dissolved in 50 mL methanol and the reaction mixture was heated at 65° C. for 18 hr. After cooling to room temperature, methanol was removed under reduced pressure. The residue was poured into 2 L tert.butylmethyl ether with stirring and then the mixture was allowed to stand for 6 hr. The white precipitate thus formed was filtered and was dried at 40° C. under vacuum for 24 hr yielding 68 g (3-chloropropyl)decylpiperidinium bromide as a light yellow solid.

Alkylation of crosslinked poly(diallylmethylamine) with (3-chloropropyl)decylpiperidinium bromide The 3% crosslinked poly(diallylmethylamine) of Example 7 (5 g) and 32 g (3-chloropropyl) decylpiperidiniumammonium bromide were dispersed in 150 mL deionized water and the reaction mixture was heated to 70° C. with stirring for 15 minutes. 2 g 50% aqueous solution of NaOH was then added to the reaction mixture. After 2 hr, 1 g NaOH solution was added and the reaction mixture was allowed to stir at 70° C. for 20 hr. When the reaction mixture had cooled to 30° C., 2 mL concentrated HCl was added and the mixture was stirred for 20 minutes. The polymer was filtered off and washed with 200 mL deionized water and 200 mL methanol. The polymer particles were dispersed in 500 mL methanol and the suspension was stirred for an additional 30 minutes, then filtered. This process was repeated once and the polymer was suspended in 300 mL 2M NaCl solution. The suspension was stirred for 45 minutes and filtered. After repeating this NaCl treatment twice, the filtered polymer was suspended in 400 mL deionized water. The mixture was stirred for 30 minutes, filtered, resuspended in 400 mL deionized water and the suspension was stirred for 40 minutes. To this polymer suspension was added 1 mL concentrated HCl and the mixture was stirred for 20 minutes. The polymer was filtered off and dried in a forced air oven at 60° C., yielding 13.2 g alkylated polymer as a pale white solid which was ground and passed through a 140 mesh sieve.

Example 31

Alkylation of Crosslinked Poly(diallylmethylamine) with (4-Chlorobutyl)diethyldecylammonium bromide (4-Chlorobutyl)diethyldecylammonium bromide was prepared by the general method of Example 10 using 4-chloro-1-bromobutane and decyldiethylamine. The 3% crosslinked poly(diallylmethylamine) of Example 7 (5 g) and 22 g (4-chlorobutyl)diethyldecylammonium bromide were dispersed in 150 mL deionized water and the resulting mixture was heated to 70° C. with stirring for 15 minutes. 2 g 50 % aqueous solution of NaOH was then added to the reaction mixture. After 2 hr, 0.5 g NaOH solution was added and the reaction mixture was allowed to stir at 70° C. for 20 hr. When the reaction mixture had cooled to 30° C., 2 mL concentrated HCl was added and the mixture was stirred for an additional 20 minutes. The polymer was filtered off and washed with 200 mL deionized water and 200 mL methanol. The polymer particles were dispersed in 500 mL methanol and the suspension was stirred for 30 minutes and then filtered. This process was repeated once and the filtered polymer was suspended in 300 mL 2M NaCl solution. The suspension was stirred for an additional 45 minutes and filtered. After repeating this NaCl treatment twice, the filtered polymer was suspended in 400 mL deionized water and the mixture was stirred for an additional 40 minutes.

To this polymer suspension was added 1 mL concentrated HCl and the mixture was stirred for 20 minutes. The polymer was filtered off and dried in a forced air oven at 60° C., yielding 10.6 g alkylated polymer as a pale white solid which was ground and passed through a 140 mesh sieve.

Example 32

Alkylation of Crosslinked Poly(diallylmethylamine) with Varying Amounts of (3-Chloropropyl) dimethyldodecylammonium bromide This example illustrates alkylation of the 3% crosslinked poly(diallylmethylamine) of Example 6 with different amounts of (3-chloropropyl)dimethyl-dodecylammonium bromide. For this purpose, the polymer was treated with varying mole fractions of the alkylating agent (1.0, 0.75, 0.50, 0.25 and 0.10) via the general procedure described in Example 9. Table 2 summarizes amounts of (3-chloropropyl)dimethyldodecylammonium bromide used to obtain polymers of varying degree of alkylation and yield of alkylated polymer per gram of the 3% crosslinked poly (diallylmethylamine). This g/g yield is a measure of the degree of alkylation of the polymer.

TABLE 2

Results of the alkylation of 3% crosslinked poly(diallylmethylamine) with varying amounts of (3-chloropropyl)dimethyldodecylammonium bromide ($C_{12}QC_3C_1Br$).

| Polymer used (grams) | alkylating agent used (grams) | mole frctn of alkylating agent w.r. to polymer | Yield of alkylated polymer (in grams) | Yield (g/g) |
|---|---|---|---|---|
| 5.0 | 14.25 | 1.0 | 11.3 | 2.3 |
| 5.0 | 10.7 | 0.75 | 8.3 | 1.7 |
| 5.0 | 7.1 | 0.50 | 7.0 | 1.40 |
| 5.0 | 3.6 | 0.25 | 6 | 1.20 |
| 5.0 | 1.40 | 0.10 | 5.1 | 1.02 |

Example 33

Synthesis of 1,4-butanediol diglycidyl ether Crosslinked Poly(diallylmethylamine)

33.2 g the 60% solution of poly(diallylmethylamine) (PAS-M-1, Lot #51017) was diluted with 68 mL D.I. water. While stirring, 2.8 g NaOH was added to the polymer solution. The reaction mixture was allowed to stir until all NaOH had dissolved. When the temperature of the solution has dropped to below 30° C., 1.25 g 1,4-butanediol diglycidyl ether was added and stirring continued. The reaction medium slowly became increasingly viscous and after about 45 minutes it gelled and the stirring was stopped. The polymer gel was left at room temperature for an additional 48 hours. The polymer slab was broken into smaller pieces and was dispersed in 300 mL D.I. water. The suspension was stirred for 30 minutes and was filtered. The swollen polymer particles were resuspended in 400 mL D.I. water, stirred for 1 hr and filtered. This process was repeated twice more. The filtered polymer (swollen gel) was dried in a forced air oven at 60° C. to yield 15 g of the product.

Example 34

Alkylation of 1,4-butanediol diglycidyl ether Crosslinked Poly(diallylmethylamine) with 1-bromodecane 5 g of the ground polymer (Example 33) was placed in a 500 mL 3-necked round-bottomed flask was suspended in 100 mL D.I. water. The polymer swelled significantly and was stirred with a mechanical stirrer. To this swollen gel, 12 g 1-bromodecane dissolved in 100 mL ethanol was added and the reaction mixture stirred for 10 minutes. Subsequently, 1 g 50% aqueous sodium hydroxide was added and the reaction mixture was stirred at room temperature for 40 minutes followed by an additional 0.5 g of NaOH solution after another 1.5 hr (the base addition was such as to maintain the pH between 10 and 12). The reaction mixture was allowed to stir at 75° C for an additional 18 hrs after which time heating was discontinued. After cooling to 30° C., 2 mL concentrated HCl was added and stirring for 30 minutes continued. The pH of the suspension dropped to 1.8. The polymer was filtered and washed with 250 mL D.I. water followed by 250 mL methanol. Polymer particles were suspended in 300 mL methanol and stirred for 40 minutes. After removing the solvent by filtration, the polymer was suspended in 250 mL 2M NaCl solution and stirred for an additional 40 minutes. It was filtered and this process of NaCl treatment was repeated two more times. The filtered polymer cake was washed with 250 mL D.I. water and suspended in 250 mL D.I. water. After stirring for 30 minutes it was filtered and resuspended in 400 mL D.I. water and stirred for an additional 30 minutes. 2 mL conc. HCl was added to the suspension and stirred for another 15 minutes. The pH of the suspension was found to be 2.10. After stirring for an additional 20 minutes, the polymer was filtered and dried at 60° C. in a forced air oven yielding 9 g of the alkylated polymer as a pale white solid. The polymer was ground and passed through a 140 mesh sieve.

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A method for removing bile acids from a human patient comprising the step of administering to the patient a therapeutically effective amount of a crosslinked poly (diallylarnine) polymer wherein more than 10% of the amino nitrogen atoms bear a $C_3$–$C_{24}$-alkyl group.

2. The method of claim 1 wherein the polymer is a homopolymer.

3. The method of claim 1 wherein the polymer is a copolymer.

4. The method of claim 1 wherein the polymer comprises a repeat unit of the general formula

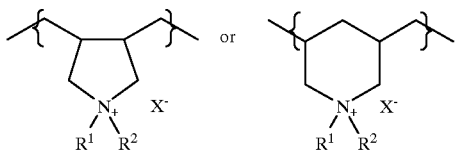

wherein $R^2$ is hydrogen, a substituted or unsubstituted $C_1$–$C_{24}$-alkyl group, a substituted or unsubstituted arylalkyl group or a substituted or unsubstituted aryl group; $R^1$ is a substituted or unsubstituted $C_3$–$C_{24}$-alkyl group; and X is a pharmaceutically acceptable anion.

5. The method of claim 4 wherein $X^-$ is a conjugate base of an acid selected from the group consisting of hydrochloric acid, hydrobromic acid, citric acid, tartaric acid, lactic acid, phosphoric acid, methanesulfonic acid, acetic acid, formic acid, maleic acid, fumaric acid, malic acid, succinic acid, maloni.c acid, sulfuric acid, L-glutamic acid, L-aspartic acid, pyruvic acid, mucic acid, benzoic acid, glucuronic acid, oxalic acid, ascorbic acid and acetylglycine.

6. The method of claim 4 wherein $R^1$ is a normal or branched $C_3$–$C_{24}$-alkyl group which is substituted by an amino group, an ammonium group, an amido group, a hydroxyl group, a sulfone group, a sulfoxide group or an alkoxy group.

7. The method of claim 4 wherein $R^1$ is an alkyl group selected from the group consisting of hexyl, heptyl, octyl, nonyl, decyl, undecyl, dodecyl, tridecyl and tetradecyl.

8. The method of claim 7 wherein $R^2$ is methyl and $R^1$ is selected from the group consisting of octyl, decyl and dodecyl.

9. The method of claim 1 wherein the polymer is characterized by a repeat unit of the general formula

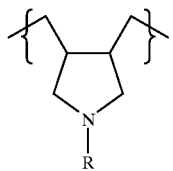 or 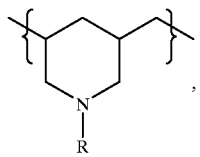

wherein R is a substituted or unsubstituted $C_3$–$C_{24}$ alkyl group.

10. The method of claim 9 wherein the alkyl group is selected from the group consisting of hexyl, heptyl, octyl, nonyl, decyl, undecyl, dodecyl, tridecyl and tetradecyl.

11. The method of claim 9 wherein the alkyl group is substituted by an amino group, an ammonium group, an amido group, a hydroxyl group, a sulfoxide group, a sulfone group or an alkoxy group.

12. The method of claim 1 wherein the polymer comprises a first monomer of the general formula

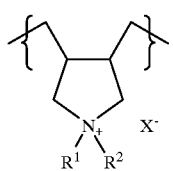 or 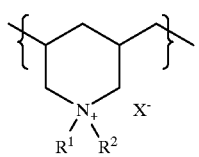

wherein $R^1$ is hydrogen, a substituted or unsubstituted $C_1$–$C_{24}$-alkyl group or a substituted or unsubstituted aryl group; $R^2$ is a substituted or unsubstituted $C_3$–$C_{24}$-alkyl group; and X is a pharmaceutically acceptable anion; and a second monomer of the general formula

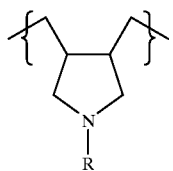 or 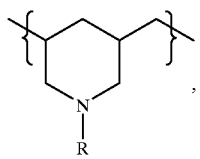

wherein R is hydrogen, a substituted or unsubstituted alkyl group or a substituted or unsubstituted aryl group.

13. The method of claim 1 wherein the polymer is a crosslinked polymer.

14. The method of claim 13 wherein the polymer is crosslinked by a multifunctional co-monomer.

15. The method of claim 14 wherein the multifunctional comonomer is selected from the group consisting of diacrylates, triacrylates, tetraacrylates, dimethacrylates, diacrylamides, dimethacrylamides, diallylacrylamides and polyvinylarenes.

16. The method of claim 15 wherein the multifunctional comonomer is selected from the group consisting of ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), bisphenol A dimethacrylate, bisphenol A diacrylate, pentaerythritol tetraacrylate, trimethylolpropane triacrylate and divinylbenzene.

17. The method of claim 14 wherein the multifunctional comonomer is a multifunctional diallylamine.

18. The method of claim 17 wherein the multifunctional diallylamine is a bis(diallylamino)alkane or a bis (diallylalkylammonio)alkane.

19. The method of claim 18 wherein the multifunctional diallylamine is 1,10-bis(diallylmethylammonio)decane dibromide.

20. The method of claim 13 wherein the polymer is crosslinked by a bridging unit selected from the group consisting of straight chain or branched, substituted or unsubstituted alkylene groups, diacylalkylene groups, diacylarene groups and alkylene bis(carbamoyl) groups.

21. The method of claim 20 wherein the bridging units are selected from the group consisting of —$(CH_2)_n$—, wherein n is an integer from about 2 to about 20; —$CH_2$—CH(OH)—$CH_2$—; —$C(O)CH_2CH_2C(O)$—; —$CH_2$—CH(OH)—O—$(CH_2)_m$—O—CH(OH)—$CH_2$—, wherein m is 2 to about 4; —$C(O)$—$(C_6H_2(COOH)_2)$—$C(O)$—; and —$C(O)NH(CH_2)_pNHC(O)$—, wherein p is an integer from about 2 to about 20.

22. A method for removing bile acids from a human patient comprising the step of administering to the patient a therapeutically effective amount of a polymer characterized by a diallylamine monomer wherein the amino nitrogen atom is substituted with an ammonioalkyl group.

23. The method of claim 22 wherein the polymer comprises a repeat unit of the general formula

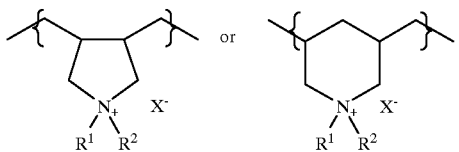

wherein $R^1$ is hydrogen, a substituted or unsubstituted $C_1$-$C_{24}$-alkyl group, a substituted or unsubstituted arylalkyl group or a substituted or unsubstituted aryl group; $R^2$ is an ammonioalkyl group; and $X^-$ is a pharmaceutically acceptable anion.

24. The method of claim 22 wherein the polymer is characterized by a repeat unit of the general formula

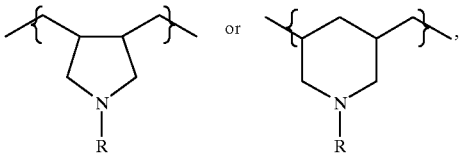

wherein R is an ammonioalkyl group.

25. The method of claim 22 wherein the ammonioalkyl group is of the general formula

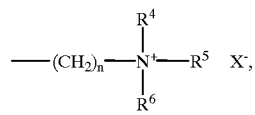

wherein n is an integer from 2 to about 20, $X^-$ is an anion, and $R^4$, $R^5$ and $R^6$ are each, independently, hydrogen or a $C_1$-$C_{24}$-alkyl group.

26. The method of claim 25 wherein at least one of $R^4$, $R^5$ and $R^6$ is a $C_6$-$C_{22}$-alkyl group.

27. The method of claim 23 wherein the polymer comprises from about 1 mole percent to 100 mole percent of the diallylamine repeat unit having an ammonioalkyl-substituted amino nitrogen atom.

28. The method of claim 22 wherein the polymer is crosslinked.

29. The method of claim 28 wherein the polymer comprises a multifunctional comonomer.

30. The method of claim 29 wherein the multifunctional monomer is selected from the group consisting of diacrylates, dimethacrylates, diacrylamides, dimethacrylamides and polyvinylarenes.

31. The method of claim 30 wherein the multifunctional comonomer is selected from the group consisting of is ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), bisphenol A dimethacrylate, bisphenol A diacrylate, diallylacrylamide and divinylbenzene.

32. The method of claim 28 wherein the multifunctional comonomer is a multifunctional diallylamine.

33. The method of claim 32 wherein the multifunctional diallylamine is a bis(diallylamino)alkane or a bis(diallylalkylammonio)alkane.

34. The method of claim 33 wherein the multifunctional diallylamine is 1,10-bis(diallylmethylammonio)decane dibromide.

35. The method of claim 28 wherein the polymer is crosslinked by bridging units selected from the group consisting of straight chain or branched, substituted or unsubstituted alkylene groups, diacylalkylene groups, diacylarene groups and alkylene bis(carbamoyl) groups.

36. The method of claim 35 wherein the bridging units are selected from the group consisting of —$(CH_2)_n$—, wherein n is an integer from about 2 to about 20; —$CH_2$—CH(OH)—$CH_2$—; —$C(O)CH_2CH_2C(O)$—; —$CH_2$—CH(OH)—O—$(CH_2)$—O—CH(OH)—$CH_2$—, wherein n is 2 to about 4; —$C(O)$—$(C_6H_2(COOH)_2)$—$C(O)$—; and —$C(O)NH(CH_2)_pNHC(O)$—, wherein p is an integer from about 2 to about 20.

37. The method of claim 1 wherein more than 20% of the amino nitrogen atoms bear a $C_3$-$C_{24}$-alkyl group.

* * * * *

UNITED STATES PATENT AND TRADEMARK OFFICE
CERTIFICATE OF CORRECTION

PATENT NO. : 6,203,785 B1
DATED : March 20, 2001
INVENTOR(S) : Stephen Randall Holmes-Farley, Pradeep K. Dhal, John S. Petersen It is certified that error appears in the above-identified patent and that said Letters Patent is hereby corrected as shown below:

Column 25, claim 4,
Line 43, delete "X" and insert -- $X^-$ --.

Column 25, claim 5,
Line 51, delete "maloni.c" and insert -- malonic --.

Column 26, claim 12,
Line 32, delete "X" and insert -- $X^-$ --.

Column 28, claim 31,
Line 24, delete the word "is".

Column 28, claim 36,
Lines 46 and 47, delete the formula "-$CH_2$-CH(OH)-O-($CH_2$)-O-CH(OH)-$CH_2$-" and insert -- -$CH_2$-CH(OH)-O-$(CH_2)_n$-O-CH(OH)-$CH_2$- --.

Signed and Sealed this

Twentieth Day of November, 2001

Attest:

NICHOLAS P. GODICI
Attesting Officer
Acting Director of the United States Patent and Trademark Office